United States Patent [19]
Lilja et al.

[11] Patent Number: 5,614,372
[45] Date of Patent: Mar. 25, 1997

[54] EARLY DETECTION OF PROSTATE CANCER (CAP) BY EMPLOYING PROSTATE SPECIFIC ANTIGEN (PSA) AND HUMAN GLANDULAR KALLIKREIN (HGK-1)

[76] Inventors: Hans Lilja, Holländarevägen 28, 236 34 Höllviken; Åke Lundwall, Mellanvångsvägen 5, 223 55 Lund, both of Sweden; Janita Lövgren, Valtaojantie 34, 20810 Turku, Finland

[21] Appl. No.: 394,033

[22] Filed: Feb. 24, 1995

[51] Int. Cl.$^6$ .................... G01N 33/574; G01N 33/53
[52] U.S. Cl. .................... 435/7.23; 435/7.4; 435/7.92; 435/7.94; 435/7.95; 436/64; 436/813
[58] Field of Search .................... 435/7.23, 7.4, 435/7.92, 7.94, 7.95; 436/64, 813

[56] References Cited

U.S. PATENT DOCUMENTS 4,446,122  5/1984  Chu et al. .................... 435/4

FOREIGN PATENT DOCUMENTS

| | | |
|---|---|---|
| 0160228 | 11/1985 | Germany . |
| 62-46263 | 2/1987 | Japan . |
| 0196845 | 10/1986 | United Kingdom . |
| WO92/01936 | 2/1992 | WIPO . |

OTHER PUBLICATIONS

Vihinen, M., "Modeling of Prostate Specific Antigen and Human Glandular Kallikrein Structures," Biochem Biophys Res Commun, vol. 204, No. 3, pp. 1251–1256, Nov. 15, 1994.

Patent Abstracts of Japan 11:233, p. 600, Abstract of Japan No. 62–46263, published on 28 Feb. 1987.

Dialog Information Service, Accession No. 88–296065/42, of Japan No. 62–46263, published 28 Feb. 1987.

Dialog Information Service, Accession No. 87–097947/14, Abstract of Japan No. 62–46263, published 28 Feb. 1987.

Chu, T.M. et al., "Circulating Antibody to Prostate Antigen in Patients with Prostatic Cancer," Ann. NY Acad. Sci. 417:383–389 (1983).

Watt, K.W.K. et al., "Human Prostate-Specific Antigen: Structural and Functional Similarity with Serine Proteases," Proc. Nat. Acad. Sci. USA 83:3166–3170 (1986).

Lilja, H., "A Kallikrein-Like Serine Protease in Prostatic Fluid Cleaves the Predominant Seminal Vesicle Protein," J. Clin. Invest. 76:1899–1903 (1985).

Lilja, H., "Prostate-Specific Antigen in Serum Occurs Predominantly in Complex with $\alpha_1$–Antichymotrypsin," Clin. Chem. 37:1618–1625 (1991).

Christenson, A. et al., "Serum Prostate Specific Antigen Complexed to $\alpha$–Antitrypsin as an Indicator of Prostate Cancer," J. Urol. 150:100–105 (1993).

Henttu, P. et al., "Prostate-Specific Antigen and Human Glandular Kallikrein: Two Kallikreins of the Human Prostate," Ann. Med. 26:157–164 (1994).

Finlay, J.A. et al., "Development of an Immunoassay for Human Glandular Kallikrein," 1994 Fall Meeting Abstract Form, Society for Basic Urologic Research (Sep. 1994).

Primary Examiner—Toni R. Scheiner
Attorney, Agent, or Firm—Venable, Baetjer, Howard & Civiletti, LLP

[57] ABSTRACT

The invention relates to a bioaffinity assay of prostate-specific antigen (PSA) comprising the measurement of either the concentration of total PSA (PSA-T), the concentration of free form of PSA (PSA-F) or the concentration of PSA complexed to alpha-1-antichymotrypsin (PSA-ACT), PSA-T being the sum of PSA-F and PSA-ACT. According to the invention, additionally the concentration of human glandular kallikrein (hGK-1) is measured. The concentrations of PSA-T and hGK-1 can be measured in one single assay or in separate assays. The sum of the concentrations of PSA-T and hGK-1 is used to determine the ratio a) PSA-F/(PSA-T+hGK-1) and/or b) PSA-ACT/(PSA-T+hGK-1). Both of these ratios are shown to have clinical utility for the discrimination of prostate cancer and benign prostatic hyperplasia.

35 Claims, 7 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:1:

TATGGATCCC ATGTGGGTCC CGGTTGTC                                28

( 2 ) INFORMATION FOR SEQ ID NO:2:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:2:

GTGGTAGCAC CGGTTGGGGA TTCCTAGGTA T                            31

( 2 ) INFORMATION FOR SEQ ID NO:3:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:3:

TATGGATCCC ATGTGGGACC TGGTTCTC                                28

( 2 ) INFORMATION FOR SEQ ID NO:4:

( i ) SEQUENCE CHARACTERISTICS:
    ( A ) LENGTH: 30 base pairs
    ( B ) TYPE: nucleic acid
    ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:4:

TGGTAGCGTC GGTTGGGGAT TCTTAGGTAT 30

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Homo sapiens     ( x i ) SEQUENCE DESCRIPTION: SEQ ID NO:5:

AGCCTCCTGA AGAATCG 17

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Homo sapiens     ( x i ) SEQUENCE DESCRIPTION: SEQ ID NO:6:

GCCTACGACT CATCCTGA 18

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Homo sapiens     ( x i ) SEQUENCE DESCRIPTION: SEQ ID NO:7:

CCTTAGACCA GATCAAG 17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Homo sapiens     ( x i ) SEQUENCE DESCRIPTION: SEQ ID NO:8:

GTCTACAACA CTTCCAG      17

EARLY DETECTION OF PROSTATE CANCER (CAP) BY EMPLOYING PROSTATE SPECIFIC ANTIGEN (PSA) AND HUMAN GLANDULAR KALLIKREIN (HGK-1)

FIELD OF THE INVENTION

This invention relates to a bioaffinity assay for the early detection of prostate cancer (CAP) by employing prostate specific antigen (PSA) and human glandular kallikrein (hGK1).

INTRODUCTION AND BACKGROUND OF THE INVENTION

The publications and other materials used herein to illuminate the background of the invention, and in particular, cases to provide additional details respecting the practice, are incorporated by reference.

Prostate-specific antigen (PSA) is an abundant 33 kDa glycoprotein secreted by the epithelial cells of the prostate (Brawer, Acta Oncol 1991; 30:161–8). The concentration of PSA in serum is normally very low but known to frequently increase above normal (i.e. 4 µg/L) in prostate cancer (CAP) patients. Therefore, immunoassys measuring the serum PSA are routinely used to monitor disease progress and relapse of CAP after removal of prostate (Brawer et al. Urology 1989; 5(suppl):11–6, Oesterling J Urol 1991; 145:907–23). However, the specifity of PSA assays for cancer detection is limited by the fact that levels above normal are found also in 30–50% of all patients with benign prostatic hyperplasia (BPH) (Stamey et al. New Engl J Med 1987; 317:909–16, Hudson et al. J Urol 1989; 142:1011–7). Serum concentrations of PSA inbetween 4–20 µg/L are particularly common in BPH patients and in patients presenting with organ confined, potentially curable CAP. This reduces the utility of the PSA assay in early diagnosis of prostate cancer.

PSA is a serine protease of the glandular kallikrein family and occurs in serum predominantly in complex with the serine protease inhibitor alpha-1-antichymotrypsin (ACT) (Lilja et al. Clin Chem 1991; 37:1618–25). A small amount of PSA circulates in a free, non-complexed form despite a large excess of ACT in serum (Lilja et al. 1991). Most commercial PSA assays detect both free PSA and PSA-ACT complex which constitutes the total PSA fraction (PSA-T). However, all assays do not detect the two forms with equal potency (Stamey et al. J Urol 1994; 152:1–5). This might affect the ability to detect CAP as it has been shown that the proportion of PSA-ACT complex form is higher in serum of CAP patients compared to those with BPH (Stenman et al. Cancer Res 1991; 51:222–6, Christensson et al. J Urol 1993; 150:100–5). This is consistent with the detection of lower free-to-total PSA ratios in CAP than in BPH (Christensson et al. 1993). The reported data also show that specific measurements of the different PSA forms improve the early diagnosis of CAP.

Large amounts of PSA are produced by the glandular epithelium of the human prostate and secreted into the seminal fluid. Low concentrations of PSA are usually found in the general circulation. The serum concentration of PSA is increased in various disease states of the prostate, especially in CAP. PSA measured by immunoassays is the predominant marker in the monitoring of CAP, mainly due to high correlation with tumor volume. The American Cancer Society has recently recommended (Kramer et al. Ann Intern Med 1993; 119:914–23) that determinations of PSA combined with digital rectal examination should be applied to men over 50 years to improve the early detection of CAP. However, the diagnostic potential of PSA measurements in serum is limited by the fact that PSA levels also are elevated in many subjects with BPH. Several improvements have been suggested to enhance the diagnostic specificity of serum PSA determinations.

Experiments designed to detemine the sequence of 5' end of PSA mRNA revealed that the prostate expresses another highly similar gene, which was identified as hGK-1 (Chapdelaine et al. FEBS Lett 1988; 236:205–8). Both PSA and hGK-1 have gene structures shared by all tissue kallikreins. Their coding sequences are 85% similar, their introns 79–86% similar and their promoter regions 91% similar (Lundwall, Biochem Biophys Res Commun 1989; 161:1151–9, Riegman et al. Biochem Biophys Commun 1989; 159:95–102, Scheidlich et al. Clin Exp Pharmacol Physiol 1988; 15:339–44). The similarity between PSA and the predicted hGK-1 protein is very pronounced and higher than that between either PSA and KLK1 (kallikrein 1) or hGK-1 and KLK1. The prostatic expression of hGK-1 has been shown to be restricted to the secretory epithelial cells, and may be 10–50% lower than that of PSA as shown by the prostate levels of hGK-1 and PSA mRNA, respectively (Young et al. Biochemistry 1992; 31:818–24). So far, the prostate is the only identified location of hGK-1 gene expression. Thus, although the hGK-1 gene is expressed in the same prostatic epithelial cell as the PSA gene, the predicted hGK-1 protein remains to be characterized in vivo. However, the coding sequences of hGK-1 predict a 261 amino acid preprotein which would give rise to a mature glycoprotein of 237 residues.

PSA is a 33 kDa glycoprotein and the mature protein consists of 237 amino acids (Lundwall & Lilja, FEBA Lett 1987; 214:317–22, Riegman et al. Biochem Biophys Res Commun 1988; 155:181–8, Henttu et al. Biochem Biophys Res Commun 1989; 160:903–10). The amino acid sequence of mature PSA has also been confirmed by analysis of purified protein (Schaller et al. Eur J Biochem 1987; 170:111–20, Watt et al. Proc Natl Acad Sci USA 1986; 83:3166–70). The hGK-1 amino acid sequence predicts one asparagine-linked glycosylation site, but at a different position when compared to PSA. The hGK-1 protein remains to be isolated and characterized.

Figure 1:
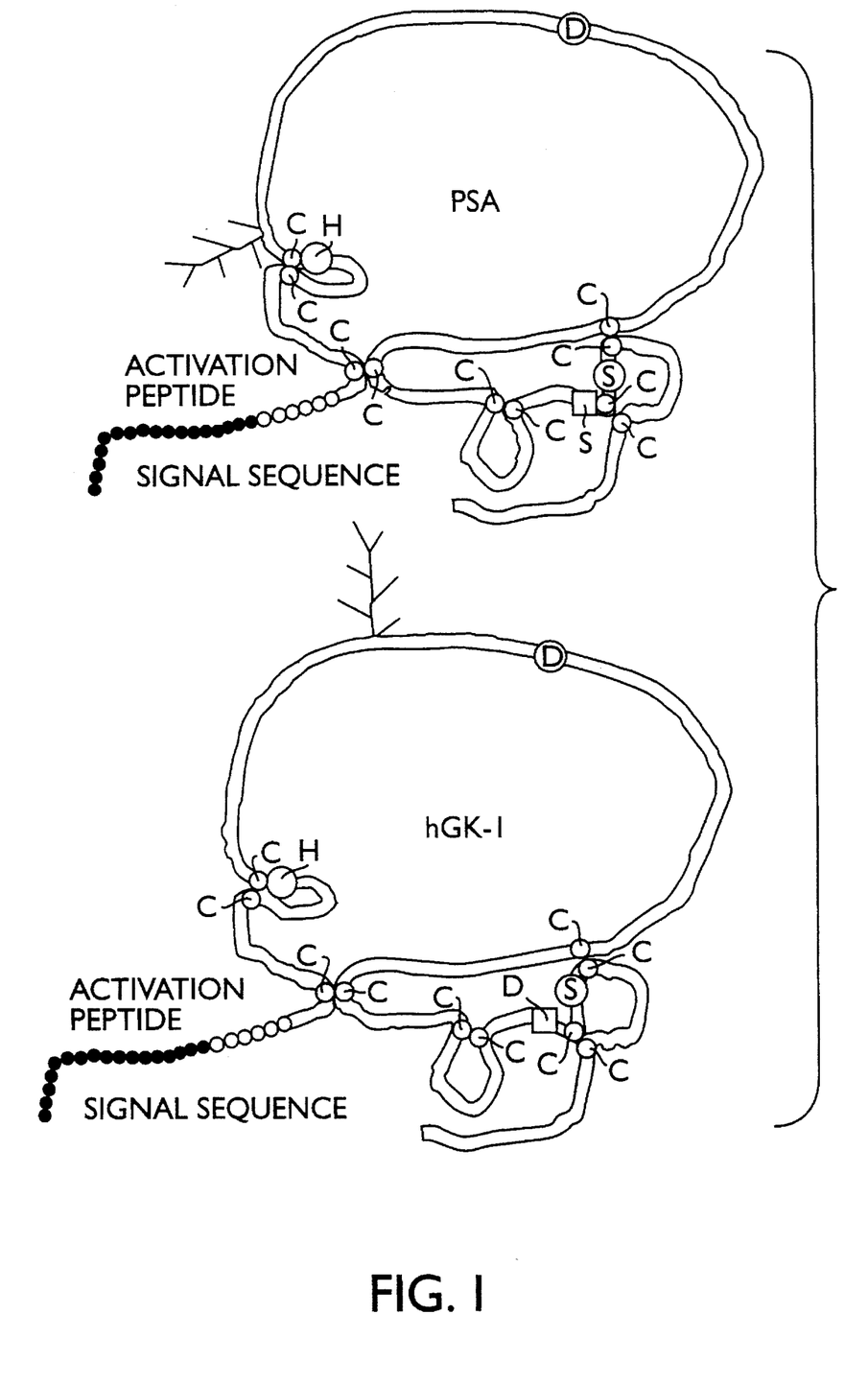

Certain structural features of PSA and the putative hGK-1 protein are shown in FIG. 1 (Henttu et al. Ann Med 1994; 26:165–71). It is likely that the three-dimensional structures of PSA and hGK-1 are very similar as both proteins retain the 10 cystein residues involved in the folding of kallikrein. There are six regions in PSA and hGK-1 polypeptide chains where 15 consecutive amino acids are identical. Therefore, it is very likely that PSA and hGK-1 share antigenic epitopes that are exposed in both proteins, as these regions also span hydrophilic regions in the proteins (Henttu et al. 1989).

In the present invention we have produced recombinant hGK-1 and PSA in vitro. The structures of the expressed proteins have been confirmed. Epitope maps for both proteins have been constructed employing a wide selection of monoclonal antibodies previously raised and characterized against PSA. Monoclonal antibodies were identified that share common antigenic epitopes on both PSA and hGK-1 in addition to monoclonal antibodies that recognize epitopes on PSA only. The identified monoclonal antibodies were used to design assays to measure total PSA+hGK-1 and total PSA alone. Serum samples from CAP and BPH patients were used to measure the concentrations of free PSA, total PSA, total PSA+hGK-1 and PSA-ACT. A clinical validation of the results was performed. Moreover, a separate assay was designed to measure only the hGK-1 concentration in serum samples. This is achieved by preincubating the sample with a PSA-specific monoclonal antibody to prevent PSA to be detected by an assay detecting both PSA and hGK-1.

Proteolytically active PSA slowly forms stable complexes in vitro with alpha-1-antichymotrypsin (ACT), alpha-2-macroglobulin, protein C inhibitor and pregnancy zone protein. In 1991 (Lilja et al. 1991) it was shown that PSA complexed to ACT is the major form of PSA in serum. An immunometric assay specific for the free non-complexed PSA was used to estimate that on average 15–20% of the total PSA concentration occurs in this form. Two-site immunometric assays of PSA-T (i.e. total PSA), PSA-ACT (i.e. PSA complexed to ACT) and PSA-F (i.e. free PSA) reported in this investigation were later used to demonstrate (Christensson et al. 1993), Lilja et al. International pat appl publ no WO 92/01936) that the ratios of PSA-F/PSA-T, being smaller in CAP than in BPH, or PSA-ACT/PSA-T, being greater in CAP than in BPH, improved the discrimination between the two groups of patients. Independent findings have later confirmed the original observation of the increased discrimination between CAP and BPH obtained by the measurement of the ratio of PSA-F/PSA-T. When, according to the present invention, the measurement of hGK-1 in addition to the different forms of PSA became possible, serum samples from CAP and BPH patients were analyzed in regard to the usefulness of hGK-1 or hGK-1 in combination with different forms of PSA in the discrimination of these two patient groups.

SUMMARY OF THE INVENTION

According to the present invention the occurence and concentration of the hGK-1 protein has for the first time been measured in human serum. Due to the specificity of the selected monoclonal antibodies, two-site immunometric assays were used to measure either the concentration of both hGK-1+PSA-T or that of PSA-T only. Another two-site immunometric assay was used to measure the concentration of PSA-F. A fourth two-site immunometric assay was used to measure the concentration of PSA-ACT (the PSA complexed to alpha-1-antichymotrypsin). An early detection of CAP and an efficient discrimination between CAP and BPH is obtained according to this invention by the determination of either the ratio PSA-F/(PSA-T+hGK-1) or the ratio PSA-ACT/(PSA-T+hGK-1). The bioffinity assay can e.g. be carried out as an immunoassay based on the use of antibodies. Alternatively, the bioaffinity assay can be performed by using genetically constructed bioaffinity components (i.e. antibody fragments) specific for the antigen(s) in question (Marks et al., J Biol Chem 1992; 267: 16007–10; Winter et al., Annu Rev Immunol 1994; 12:433–55; Owens and Young, J Immunol Methods 1994; 168: 149–165).

The sum PSA-T+hGK-1 can be measured simultaneously using antibodies or antibody fragments that recognize common isotopes on both PSA and hGK-1. Alternatively, the amounts of PSA-T and hGK-1 are measured separately after which the sum is calculated. The clinical utility of the new ratios (i.e. PSA-F/(PSA-T+hGK-1), or PSA-ACT/(PSA-T+ hGK-1) for the discrimination between CAP and BPH is similar or possibly increased when compared to the usefulness in measurements of the ratio PSA-F/PSA-T or PSA-ACT-/PSA-T, respectively. Therefore, the ratio PSA-F/ (PSA-T+hGK-1) as determined according to the invention is also smaller in CAP than in BPH while the ratio PSA-ACT/ (PSA-T+hGK-1) is greater in CAP than in BPH.

BRIEF DESCRIPTION OF THE DRAWINGS

FIG. 1 shows certain structural features of PSA and hGK-1 enzymes. Amino acids that differ between the mature PSA and hGK-1 polypeptide chains are shown by black circles in the hGK-1 figure. The positions of the five disulphide bonds (shown by the letter C within a circle) and the positions of the active site residues (letters within circles) are based on the typical structure of serine proteases. The active site residues considered to be involved in determining the substrate specificities of PSA (i.e. serine 183) and hGK-1 (i.e. aspartate 183) are indicated by a letter within a box. The glycosylation sites (i.e. asparagine 45 in PSA and asparagine 78 in hGK-1) are indicated by branched structures. The figure is modified from Bilhartz et al., Urology 1991; 38:95–102 and no attempt has been made to illustrate the three-dimensional folding of the polypeptide chains.

Lane 1: purified PSA from seminal plasma
Lane 2: recombinant PSA
Lane 3: recombinant hGK-1

FIG. 3 shows the epitope maps for PSA, PSA-ACT and hGK-1. Overlapping circles indicate no sandwich formation. Touching circles indicate interfering sandwich formation. Separate circles indicate independent epitopes.

FIGS. 4A to 4C illustrate the bioaffinity assay (immunoassay) design for specific detection of hGK-1 and its complexes:

FIG. 4A shows the blocking reaction. The sample containing PSA, hGK-1 and their complexes are reacted with an excess of a Mab A5 specifically recognizing PSA alone. This serves to totally block PSA from participating in the subsequent immunoreactions. The blocking step is carried out in a well coated with streptavidin.

FIG. 4B shows the specific capture of hGK-1. A biotinylated Mab B6, equally well recognizing PSA and hGK-1 (and their complexes), is added to capture hGK-1 to the streptavidin surface. Reaction between Mab B6 and PSA is blocked by the presence of Mab A5. After completed incubation, the wells are washed. This completely removes PSA and its complexes.

FIG. 4C shows the detection of hGK-1. An excess of labelled antibody Mab B1 (recognizing both PSA and hGK-1 and their complexes) is added to detect the hGK-1 bound to the streptavidin surface through Mab B6.

DETAILED DESCRIPTION OF THE INVENTION

1. Production of recombinant proteins
Materials

The DNA coding for PSA was derived from a PSA cDNA clone in pGEM (Lundwall and Lilja, 1987). The hGK-1 cDNA was cloned as described by Young et al. 1992 and ligated into the plasmid vector puc 19. The vectors pSFV1, pSFV3, pSFV3-lacZ and pSFV-Helper 2 were a gift from P.

Liljeström (Liljeström and Garoff, Biotechnology 1991; 9:1356–61). The PCR primers 5'-PSAV3:5'-TAT GGA TCC CAT GTG GGT CCC GGT TGT C-3' (SEQ. ID NO:1), 3'-PSA: 3'-TAT GGA TCC TTA GGG GTT GGC CAC GAT GGT G-5' (SEQ. ID NO:2), 5'-hGk-1V3: 5'-TAT GGA TCC CAT GTG GGA CCT GGT TCT C-3' (SEQ. ID NO.3), 3'-hGK-1: 3'-TAT GGA TTC TTA GGG GTT GGC TGC GAT GGT-5' (SEQ. ID NO.4) and the sequencing primers SP1 and SP2 (Liljeström and Garoff, 1991), 5'-PSAM: 5'-AGC CTC CTG AAG AAT CG-3' (SEQ. ID NO:5), 3'-PSAM: 3'-TGA CCT TCA CAG CAT CCG-5' (SEQ ID NO:6), 5'-hGK1M: 5'-CCT TAG ACC AGA TGA AG-3' (SEQ ID NO:7) and 3'-hGK1M: 3'-GAC CTT CAC AAC ATC TG-5' (SEQ. ID NO:8) were synthesized on an Applied Biosystems oligo-nucleotide synthesizer. Molecular biology reagents and enzymes were obtained from Appligene, Boehringer Mannheim, Pharmacia Biotech or Promega. Sequencing was done with PRISM Sequenase Terminator (Applied Biosystems, Foster City, Calif.). The western blotting reagents were from Amersham (Buckinghamshire, England).

Equipment

Agarose gel electrophoresis was run with an equipment from Appligene. The PCR was run with a MiniCycler (SDS, Falkenberg, Sweden). The sequence gels were run and analyzed with the 373 DNA Sequencer from Applied Biosystems. The electroporations were done with Gene Pulser (Bio-Rad, Richmond, Calif.). Sodium dodecyl sulphate polyacrylamide gel electrophoresis (SDS-PAGE) was run with the Mini PROTEAN II system from BioRad. Western blotting of proteins was done with Semi Dry Blotter II from Kem En Tec.

Construction of pSFV3-PSA and pSFV3-hGK1

The work with DNA was done with conventional techniques described by Sambrook et al. A Laboratory Manual, 1989 2nd edn., Cold Spring Harbor Laboratory, Cold Spring Harbor, N.Y. if not otherwise stated. The bacterial cells used in the work were *E. coli* DH5alfa. Competent cells were prepared as described in BioRads Gene Pulser manual. The DNA coding for preproPSA was amplified with polymerase chain reaction (PCR) from pGEM-PSA with primers 5'PSAV3 and 3'-PSA and the DNA coding for preprohGK1 from pUC19-hGK1 with primers 5'-hGK1V3 and 3'-hGK1 using Pfu DNA polymerase (Stratagene, LaJolla, Calif.). The reaction consisted first of 5 cycles of denaturation at 94° C. for 50 seconds, annealing at 58° C. for 1 minute, and polymerization at 72° C. for 2 minutes followed by 25 subsequent cycles of denaturation at 94° C. for 50 seconds, annealing at 64° C. for 1 minute and polymerization at 72° C. for 2 minutes. All primers contained a BamH1 restriction site which was used to ligate the fragments into the vectors. After cutting the fragments with BamH1 they were isolated from an agarose gel with JetSorb (Genomed GmbH, Bad Oeynhausen, Germany), purified and ligated into puc18. The fragments were cut out of puc18 with BamH1, purified as before and then ligated into pSFV3. The nucleotide sequences of the final constructs were verified by DNA sequencing. The primers used in the sequence reactions were SP1, SP2, 5'-PSAM, 3'-PSAM, 5'hGK1M and 3'-hGK1M.

Expression of recombinant PSA and hGK-1

Protein expression was done with Semliki Forest Virus expression system (Berglund et al. Biotechnology 1993; 11:916–920). The protocols used were from the SFV/Helper 2 gene expression system users' manual (Life Technologies, Gibco BRL). The vectors were first linearized with SpeI. The mRNA was generated in a total volume of 50 µl with 30 units SP6 polymerase from 1.5 µg of the linearized vector in a SP6 buffer containing additionally 1 mM ATP, CTP, and UTP, 0.5 mM GTP, 1 mM m7G(5')ppp(5')G and 50 units RNasin. The reaction mixture was incubated for 2 hours at 37° C. Half of the mRNA was transferred to BHK-21 cells by electroporation. The BHK-21 cells were grown in MEM (Gibco BRL) supplemented with 2 mM glutamine, 100 U/ml penicillin, 100 µg/ml streptomycin, non essential amino acids (ICN Biomedicals, Costa Mesa, Calif.) and 5% fetal bovine serum. The cells were detatched with Trypsin-EDTA, washed with PBS without $Mg^{2+}$ and $Ca^{2+}$ and suspended to a concentration of about 10×7 cells per ml. The electroporation was done by pulsing twice with 850 V/25 µF in a 0.4 cm cuvette using 0.8 ml of the cell mixture. After the electroporation the cells were suspended in 20 ml of culture medium and transferred to a culture bottle. The supernatant containing the expressed proteins was collected after 48 or 72 hours. The function of the expression system in our hands was checked by doing all the steps of the expression of PSA and hGK1 in parallel with the expression of β-galactosidase with pSFV3-lacZ (Liljeström & Garoff, 1991).

Electrophoresis and immunoblotting

The size separation of the proteins was done with SDS-PAGE run as described in the Mini-PROTEAN electrophoresis cell instruction using 12% polyacrylamide gels. The size of the expressed proteins was verified with molecular mass markers for SDS-PAGE (Pharmacia, Uppsala, Sweden) and by ECL-western blotting (Amersham, Buckinghamshire, England) using the protocol suggested by the manufacturer. The detection was done with a 0.1 µg/ml mixture of biotinylated monoclonal antibody B1 and B6 and streptavidin-horseradish peroxidase.

Verification of the protein produced

The nucleotide sequences coding for the prepro-form of the proteins and the orientation Of the DNA inserted in the pSFV3 vectors were verified by nucleotide sequencing to validate that no base substitutions had occurred during the construction of the vectors. The pSFV3-PSA codes for a 261 aa preproPSA and pSFV3-hGK1 codes for a 261 aa preprohGK1. Both constructs contained a sequence coding for an extra Met-Asp-Pro in the beginning of the proteins. The nucleotide sequence coding for hGK-1 differs from the genomic sequence reported earlier (Schedlich et al., DNA 1987; 6:429–437) at nucleotides 600 (G->A) and 663 (G->T) (relative to the initiation codon). These changes are different from those reported earlier in cDNA sequences (Riegman et al., Molecular and Cellular Endocrinology 1991; 76:181–190; Young et al., 1992). The changes do not affect the amino acid sequence that is identical to that previously reported (Schedlich et al., 1987).

Size of recombinant PSA and hGK1

Figure 2:
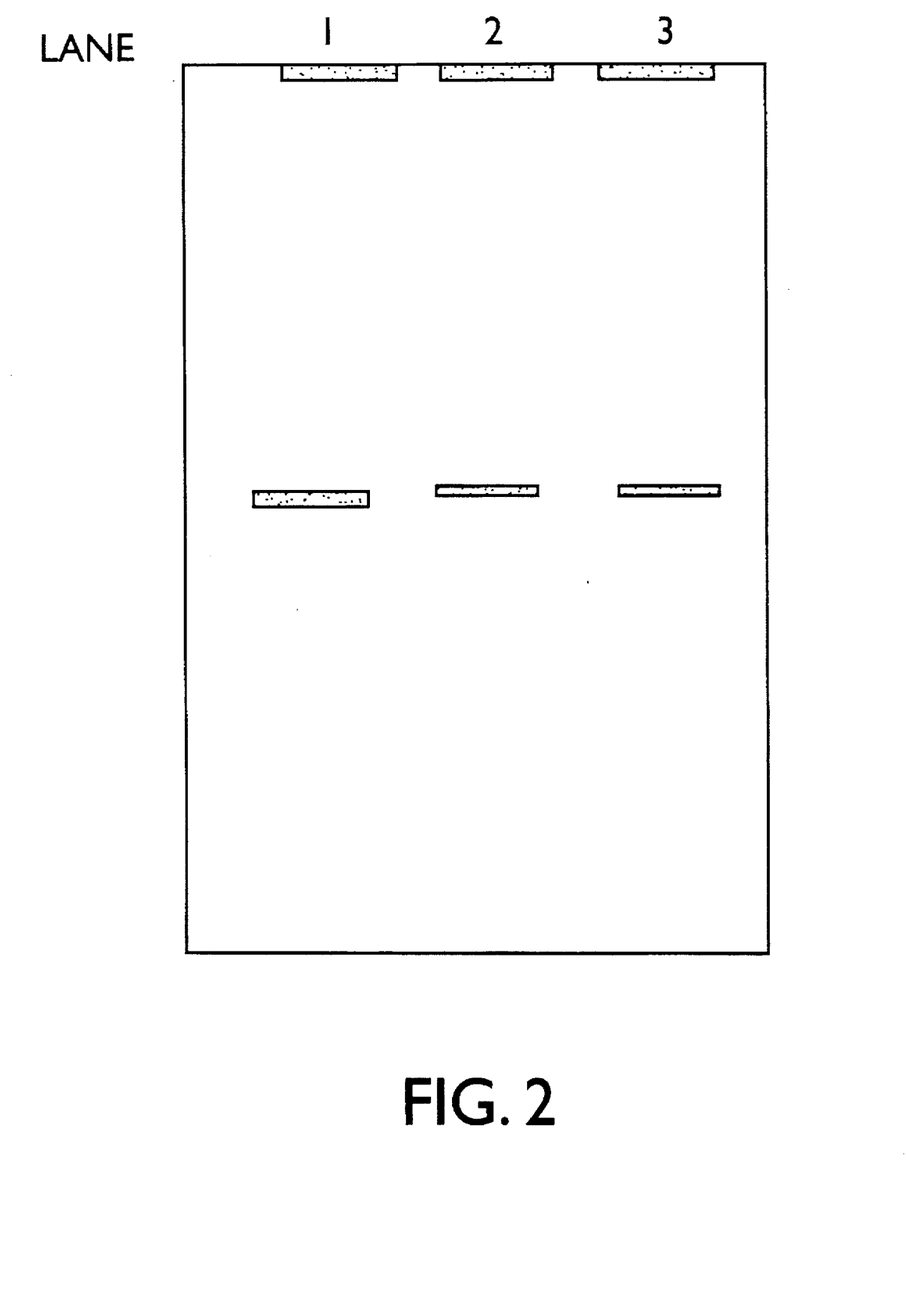
FIG. 2 illustrates an ECL Western blot detection of the proteins with 0.1 µg/ml of B1+B6 monoclonal antibodies. The figure is drawn according to the original experimental data.

The size of the proteins was determined by western blot after SDS-PAGE using monoclonal antibodies B1 and B6. The size of recombinant PSA and hGK-1 was identical to that of PSA purified from seminal plasma (FIG. 2).

2. Epitope mapping

Figure 3:
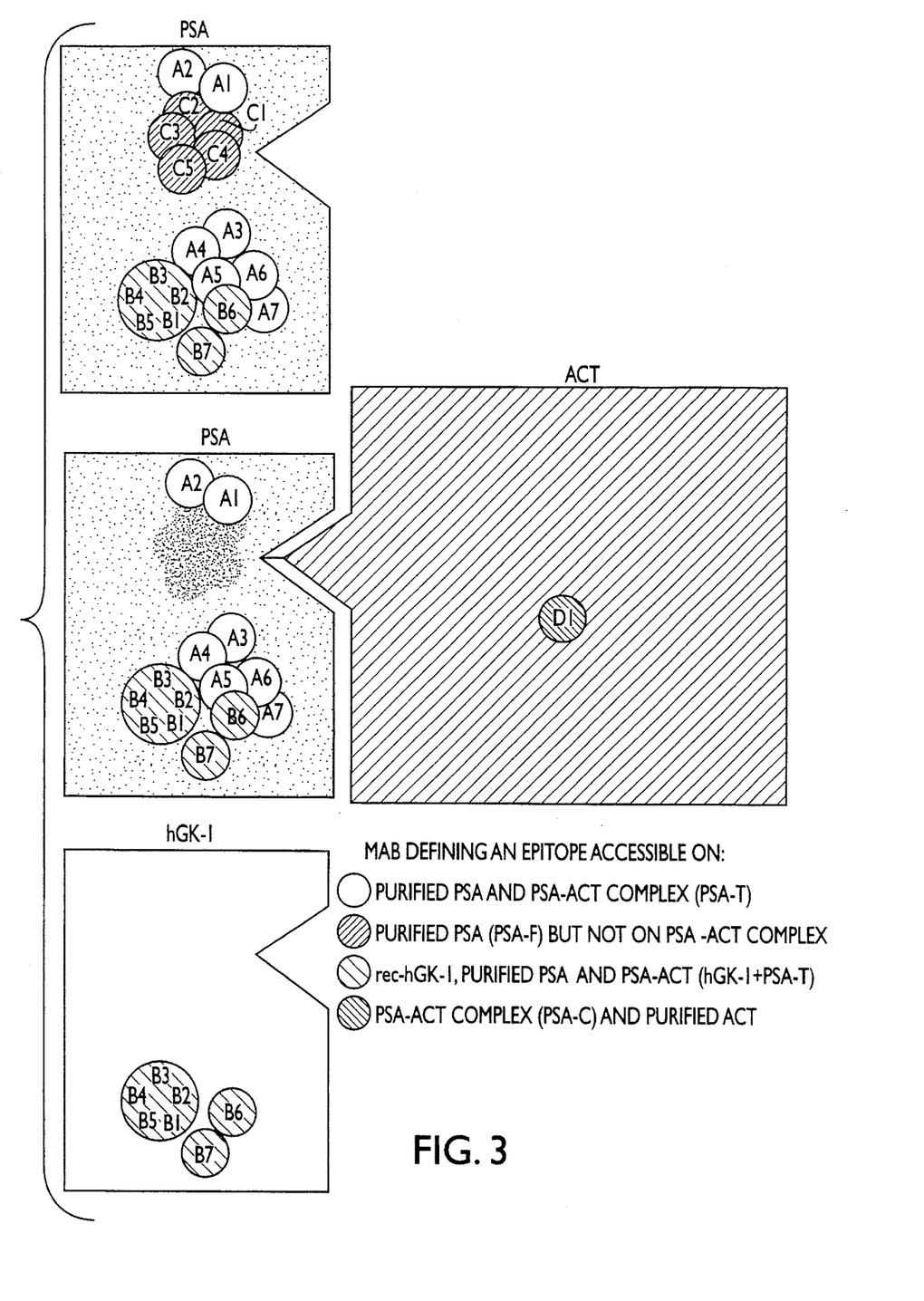

Epitope mapping studies using previously described procedures (Pettersson et al. Clin Chem in press) were carried out by the analysis of the immunodetecting capacity of every possible combination of the available monoclonal anti PSA antibodies: one Mab being immobilized to the microtitration well and the other labelled with Eu-chelate, by using as antigen either purified PSA (isolated from seminal fluid) or recombinantly produced PSA or hGK-1. After a first qualitative test (no binding versus detectable binding) affinity constants were determined according to a previously reported protocol (Pettersson et al. Clin Chem in press) for the PSA-Mabs recognizing rhGK-1. The data are compiled in Table I. The respective epitope maps for the monoclonal antibodies recognizing epitopes on PSA, PSA-ACT and hGK-1 are shown in FIG. 3. Six of the tested monoclonal anti-PSA antibodies (B1, B2, B3, B4, B6 and B7) were found to be equally reactive with rhGK-1, rPSA and PSA purified from seminal fluid. One additional monoclonal antibody (B5) also recognized rhGK-1 but the affinity for hGK-1 was significantly lower than that for PSA. In total, seven of the tested monoclonal anti-PSA antibodies (A1–A7) recognized epitopes that were unique to PSA and not shared with rhGK-1. These epitopes are exposed on both free PSA and on PSA-ACT, five (C1–C5) recognized epitopes unique to PSA that were exposed on free PSA alone, and seven (B1–B7) recognized epitopes available on both free PSA and PSA-ACT that were common to hGK-1. The specificities of the monoclonal antibodies are given in Table 1.

TABLE 1

Affinity constants and specificity of Mabs

| antibody | PSA | PSA-ACT | hGK-1 | specificity |
|---|---|---|---|---|
| A1 | $3 \times 10^9$ | $4 \times 10^8$ | | PSA-T |
| A2 | $2 \times 10^9$ | n.d. | | " |
| A3 | $2 \times 10^7$ | $1 \times 10^7$ | | " |
| A4 | $4 \times 10^9$ | n.d. | | " |
| A5 | $7 \times 10^8$ | $4 \times 10^8$ | | " |
| A6 | $6 \times 10^7$ | $3 \times 10^7$ | | " |
| A7 | $8 \times 10^8$ | $7 \times 10^8$ | | " |
| B1 | $4 \times 10^{10}$ | $2 \times 10^{10}$ | $1 \times 10^{10}$ | hGK-1 + PSA-T |
| B2 | $5 \times 10^8$ | $5 \times 10^8$ | $2 \times 10^9$ | " |
| B3 | $6 \times 10^8$ | n.d. | $7 \times 10^8$ | " |
| B4 | $5 \times 10^8$ | $5 \times 10^8$ | $2 \times 10^9$ | " |
| B5 | $2 \times 10^{10}$ | $8 \times 10^9$ | $3 \times 10^9$ | " |
| B6 | $3 \times 10^9$ | $2 \times 10^9$ | $3 \times 10^8$ | " |
| B7 | $2 \times 10^9$ | $2 \times 10^9$ | $2 \times 10^9$ | " |
| C1 | $3 \times 10^{10}$ | | | PSA-F |
| C2 | $1 \times 10^9$ | | | " |
| C3 | $2 \times 10^8$ | | | " |
| C4 | $5 \times 10^9$ | | | " |
| C5 | $2 \times 10^8$ | | | " |
| D1 | | $1 \times 10^9$ | | PSA-C and ACT |

3. Assays for specific determination of PSA-F, PSA-T, PSA-T+hGK-1 and PSA-ACT using selected monoclonal antibody combinations Based on the information obtained from the PSA and hGK-1 epitope maps and the determinations of the affinity constants, two immunofluorometric assays were constructed. The combination of monoclonal antibody B1 on the solid phase with monoclonal antibody B6 as a tracer co-detects PSA and hGK-1 (PSA-T+hGK-1). The combination of monoclonal antibody A1 on the solid phase with monoclonal antibody B1 as a tracer provides specific measurements of both free PSA and PSA-ACT (PSA-T), but does not co-detect hGK-1. An additional assay was optimized using monoclonal antibody B1 on the solid phase and monoclonal antibody C2 as tracer for the specific measurement of free PSA (PSA-F). This assay did not co-detect hGK-1. It was not possible to design an assay that selectively detected the free form of PSA that also co-detected hGK-1, since all monoclonal antibodies specifically detecting the free form of PSA were unable to recognize hGK-1. Moreover separate assay was made to measure only PSA-ACT by using monoclonal antibody B1 on the solid phase and monoclonal antibody D1 as tracer. The assays were set up according to previously published procedures (Lilja et al. 1991, Pettersson et al. Clin Chem in press).

An additional assay was designed for the specific measurement of hGK-1. As no monoclonal antibody was available that would directly and exclusively recognize hGK-1 but not PSA, this assay employs a separate step to totally and specifically block the recognition of both the free form of PSA and PSA-ACT. This is achieved by addition of an excess of monoclonal antibody A5, which recognizes both the free form of PSA and PSA-ACT but does not cross-react with hGK-1. This prevents PSA from reacting in the subsequent immunofluorometric assay (biotinylated monoclonal B6 as catcher antibody/labelled monoclonal B1 as tracer antibody) which without the blocking step measures equally well PSA and hGK-1. This is due to the overlapping between the A5 and B6 epitopes (FIG. 3). An example of the detailed performance of this assay is described in FIG. 4A to 4C. A control assay to hGK-1 was performed in an identical way, but by omitting the step employing the PSA blocking monoclonal antibody A5: Assay PSA+hGK-1.

4. Discrimination between clinical BPH and CAP by the measurement of the ratio PSA-F/PSA-T, PSA-F/(PSA-T+ hGK-1) or PSA-ACT/(PSA-T+hGK-1).

Figure 5:
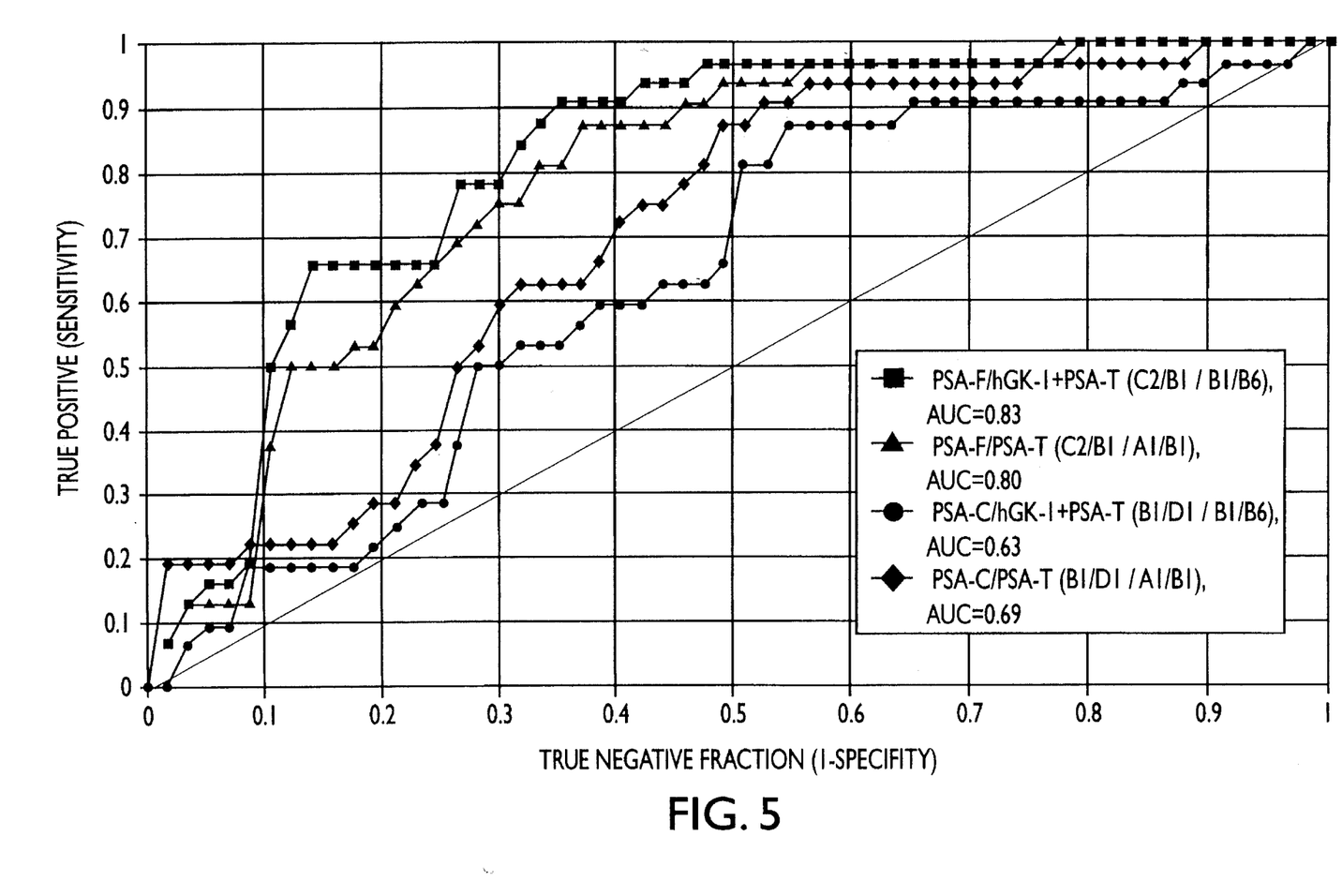
FIG. 5 shows the receiver operation characteristics (ROC) for the discrimination of male subjects without CAP (BPH+ Normal) from patients with CAP using the ratios obtained for the four different assay combinations PSA-F/(hGK-1+ PSA-T); PSA-F/PSA-T; PSA-C/(hGK-1+PSA-T) and PSA-C/PSA-T. PSA-C means the same as PSA-complexed ACT, i.e. PSA-ACT. The areas under the curves (AUC) were calculated and compared. Number of samples: BPH+Normal=57; CAP=32. PSA-T cut-off 1–20 µg/L.

57 serum samples from normal male subjects and patients with BPH and no evidence of CAP and 32 pre-treatment samples from patients with documented CAP were tested with assays for PSA-F, PSA-T, PSA-T+hGK-1 and PSA-ACT (Table 2). The respective ratios: PSA-F/PSA-T; PSA-F/(PSA-T+hGK1); PSA-ACT/PSA-T; and PSA-ACT/(PSA-T+hGK-1) were calculated for all the samples. Receiver operation characteristics (ROC) analyses were calculated for the discrimination of BPH from CAP using the ratios obtained for the four different assay combinations mentioned above (FIG. 5). The areas under the curve using ratio PSA-F/PSA-T was 0.80, using ratio PSA-F/(PSA-T+hGK-1) it was 0.83, using ratio PSA-ACT/PSA-T it was 0.69 and using ratio PSA-ACT/(PSA-T+hGK-1) it was 0.63, respectively. Thus the ratio between PSA-F/(PSA-T+hGK-1) gave the best performance while the ratio between PSA-ACT/ (PSA-T+hGK-1) gave the lowest discrimination between the patient groups. According to the results it is obvious that an assay for the measurement of PSA-T+hGK-1 is useful in the discrimination of BPH from CAP and in early detection of CAP when used in combination with the measurement of PSA-F or PSA-ACT to calculate the ratios to be used.

TABLE 2

Assays for PSA-F, PSA complexed to ACT (=PSA-C), PSA-T and PSA-T + hGK-1. PSA-T cut off level 1–20 µg.

| | µg/L | | | |
|---|---|---|---|---|
| sample | PSA-T + hGK-1 B1/B6 | PSA-T A1/B6 | PSA-F C2/B1 | PSA-C B1/D1 |
| NORMALS | | | | |
| 6 | 1.71 | 1.84 | 0.30 | 1.74 |
| 27 | 3.05 | 3.28 | 0.39 | 3.51 |
| 28 | 2.37 | 2.46 | 0.71 | 1.85 |
| 39 | 4.91 | 5.44 | 0.90 | 4.38 |
| 41 | 1.59 | 1.83 | 0.32 | 1.08 |
| 43 | 1.08 | 1.44 | 0.19 | 0.71 |
| 47 | 1.89 | 2.35 | 0.19 | 1.61 |
| 50 | 1.96 | 2.20 | 0.36 | 1.82 |
| 56 | 7.16 | 7.62 | 2.00 | 5.99 |
| 63 | 1.11 | 1.38 | 0.06 | 0.78 |
| 67 | 2.05 | 2.29 | 0.11 | 1.70 |
| 68 | 4.45 | 5.35 | 0.80 | 3.61 |
| 73 | 2.50 | 3.08 | 0.15 | 2.20 |
| 76 | 2.12 | 2.78 | 0.43 | 1.61 |
| 86 | 1.48 | 1.79 | 0.21 | 1.15 |
| 88 | 2.92 | 3.78 | 0.38 | 2.32 |
| 89 | 1.00 | 1.52 | 0.24 | 0.74 |
| 90 | 2.64 | 3.50 | 0.46 | 1.77 |

TABLE 2-continued

Assays for PSA-F, PSA complexed to ACT (=PSA-C), PSA-T and PSA-T + hGK-1. PSA-T cut off level 1–20 µg.

| sample | PSA-T + hGK-1 B1/B6 (µg/L) | PSA-T A1/B6 (µg/L) | PSA-F C2/B1 (µg/L) | PSA-C B1/D1 (µg/L) |
|---|---|---|---|---|
| 111 | 4.46 | 4.94 | 1.01 | 3.20 |
| n = | 19 | | | |
| BPH | | | | |
| 3 | 1.46 | 1.54 | 0.37 | 1.39 |
| 7 | 10.05 | 10.62 | 1.79 | 9.96 |
| 8 | 1.66 | 1.62 | 0.38 | 1.41 |
| 13 | 18.41 | 20.22 | 3.22 | 19.67 |
| 14 | 16.12 | 15.85 | 3.90 | 15.15 |
| 24 | 2.95 | 3.77 | 0.72 | 2.07 |
| 30 | 7.21 | 7.47 | 1.64 | 6.69 |
| 36 | 7.71 | 7.87 | 3.42 | 5.05 |
| 44 | 3.18 | 3.64 | 0.43 | 2.99 |
| 57 | 3.97 | 4.70 | 0.38 | 3.30 |
| 58 | 15.00 | 14.57 | 3.66 | 13.59 |
| 72 | 14.30 | 14.03 | 1.46 | 13.96 |
| 75 | 1.53 | 1.98 | 0.29 | 1.77 |
| 77 | 3.13 | 4.21 | 0.42 | 2.36 |
| 79 | 5.17 | 6.53 | 0.96 | 4.02 |
| 82 | 4.54 | 4.56 | 0.98 | 2.93 |
| 85 | 1.29 | 1.92 | 0.32 | 0.91 |
| 87 | 11.28 | 14.30 | 1.75 | 8.26 |
| 92 | 4.15 | 4.08 | 0.51 | 3.02 |
| 95 | 2.28 | 2.63 | 0.37 | 1.62 |
| 96 | 2.18 | 2.88 | 0.22 | 1.61 |
| 97 | 2.78 | 3.71 | 0.27 | 1.95 |
| 101 | 6.04 | 7.02 | 0.62 | 5.09 |
| 105 | 3.92 | 4.39 | 0.46 | 3.20 |
| 106 | 5.99 | 7.00 | 1.35 | 4.56 |
| 107 | 10.75 | 12.19 | 2.63 | 7.51 |
| 109 | 1.07 | 1.31 | 0.12 | 0.95 |
| 114 | 9.06 | 8.86 | 0.75 | 7.22 |
| 115 | 9.80 | 10.40 | 3.42 | 5.74 |
| 116 | 4.96 | 5.65 | 1.23 | 3.35 |
| 120 | 13.47 | 15.05 | 1.20 | 11.53 |
| 124 | 1.02 | 1.32 | 0.31 | 0.69 |
| 135 | 12.77 | 15.62 | 2.05 | 10.83 |
| 136 | 2.42 | 3.30 | 0.15 | 2.46 |
| 137 | 7.83 | 9.27 | 1.15 | 6.66 |
| 144 | 19.22 | 20.48 | 1.99 | 16.06 |
| 145 | 14.35 | 16.67 | 4.53 | 9.72 |
| 210 | 7.86 | 8.91 | 0.35 | 6.71 |
| n = | 38 | | | |
| CAP | | | | |
| 225 | 3.10 | 3.56 | 0.15 | 2.80 |
| 1 | 9.57 | 10.42 | 1.23 | 10.61 |
| 62 | 16.86 | 16.43 | 1.40 | 17.02 |
| 142 | 19.03 | 20.86 | 1.02 | 16.54 |
| 183 | 19.76 | 21.91 | 1.28 | 17.95 |
| 326 | 10.75 | 11.07 | 0.40 | 8.68 |
| 99 | 16.54 | 15.72 | 2.05 | 11.22 |
| 112 | 12.50 | 14.45 | 1.63 | 10.61 |
| 118 | 3.68 | 4.23 | 0.89 | 2.30 |
| 2 | 1.89 | 1.77 | 0.18 | 1.28 |
| 15 | 4.14 | 4.46 | 0.62 | 4.52 |
| 29 | 7.03 | 7.30 | 0.73 | 7.37 |
| 98 | 7.78 | 10.62 | 0.31 | 6.25 |
| 108 | 3.10 | 3.68 | 0.33 | 2.73 |
| 113 | 6.41 | 7.20 | 0.47 | 5.59 |
| 117 | 1.27 | 1.53 | 0.16 | 1.08 |
| 134 | 9.75 | 12.47 | 0.91 | 8.14 |
| 147 | 6.37 | 7.12 | 1.09 | 6.33 |
| 192 | 16.75 | 18.37 | 1.35 | 14.85 |
| 222 | 18.02 | 18.56 | 1.10 | 14.19 |
| 224 | 18.04 | 19.83 | 1.17 | 14.63 |
| 244 | 8.40 | 9.61 | 0.63 | 6.78 |
| 255 | 9.00 | 9.92 | 0.98 | 7.91 |
| 266 | 7.92 | 9.26 | 0.74 | 7.35 |
| 273 | 14.39 | 12.92 | 1.55 | 12.12 |
| 335 | 15.50 | 17.29 | 1.07 | 13.32 |
| 364 | 15.80 | 12.47 | 1.16 | 12.76 |
| 162 | 7.02 | 7.18 | 0.55 | 6.08 |
| 212 | 3.59 | 2.84 | 0.25 | 2.88 |
| 294 | 2.29 | 2.80 | 0.11 | 2.28 |
| 360 | 4.48 | 4.80 | 0.29 | 3.32 |
| 387 | 3.27 | 3.58 | 0.28 | 2.59 |
| n = | 32 | | | |

5. Determination of hGK-1 concentrations in serum samples.

Figure 4A:
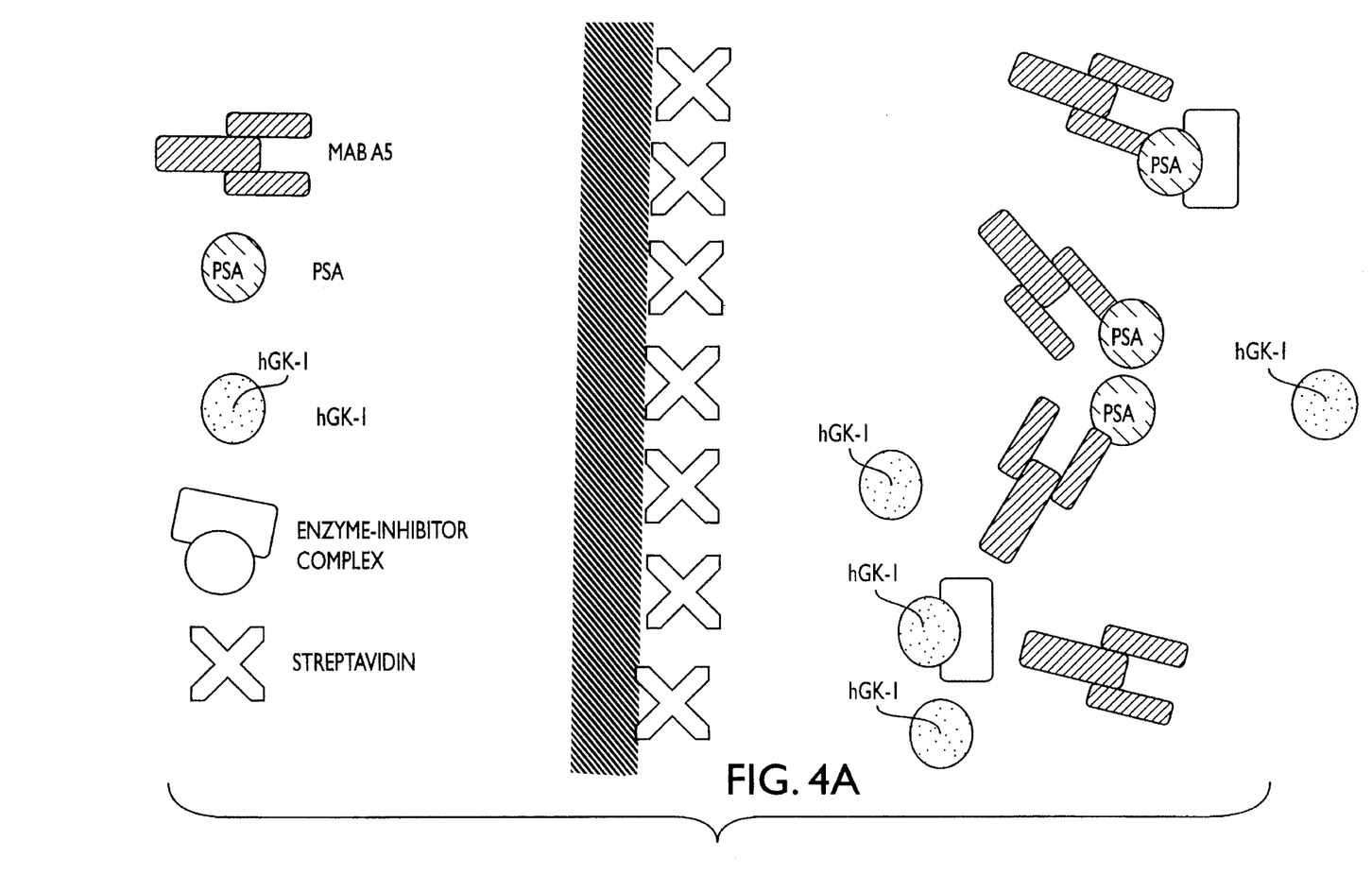
Figure 4B:
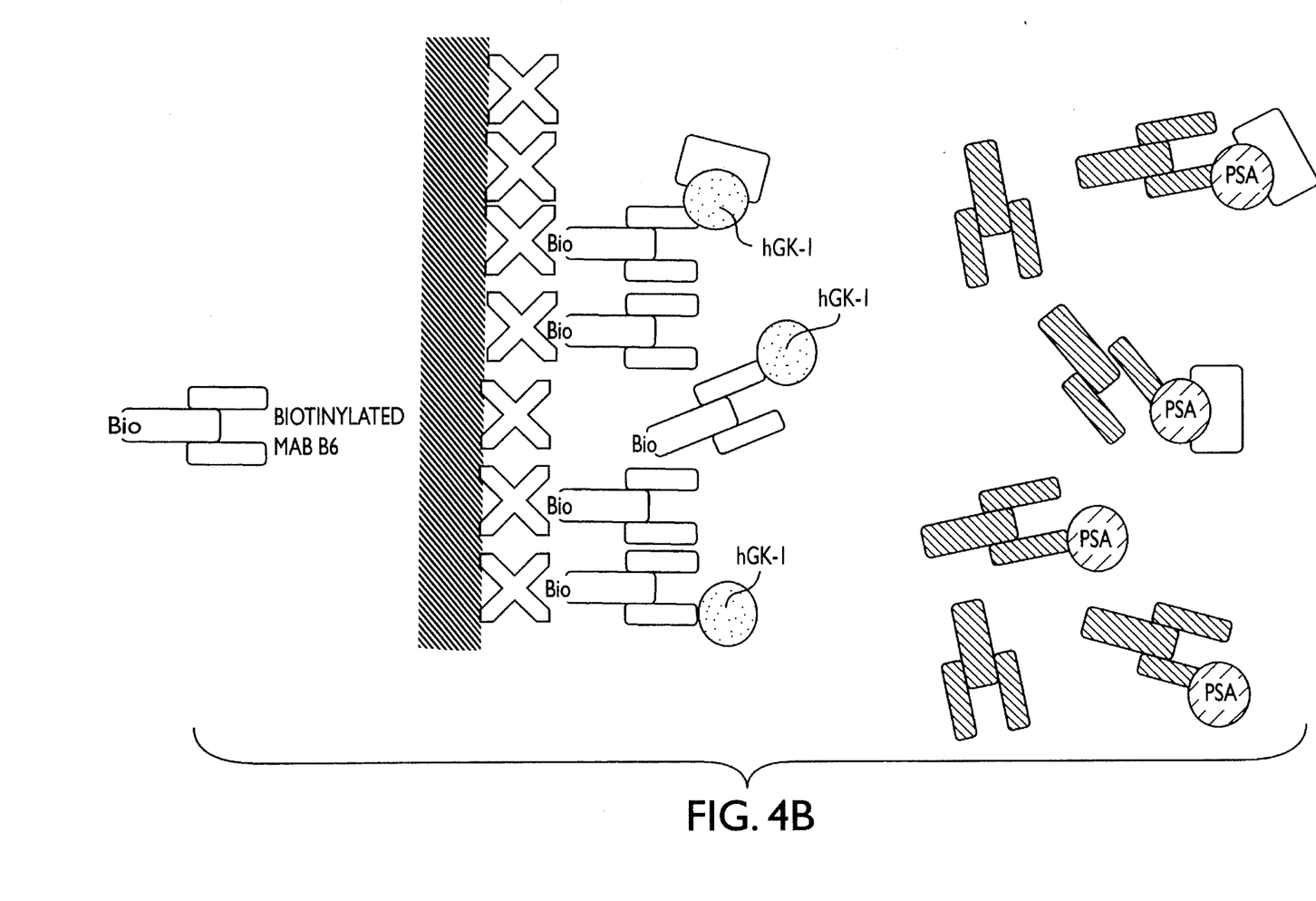
Figure 4C:
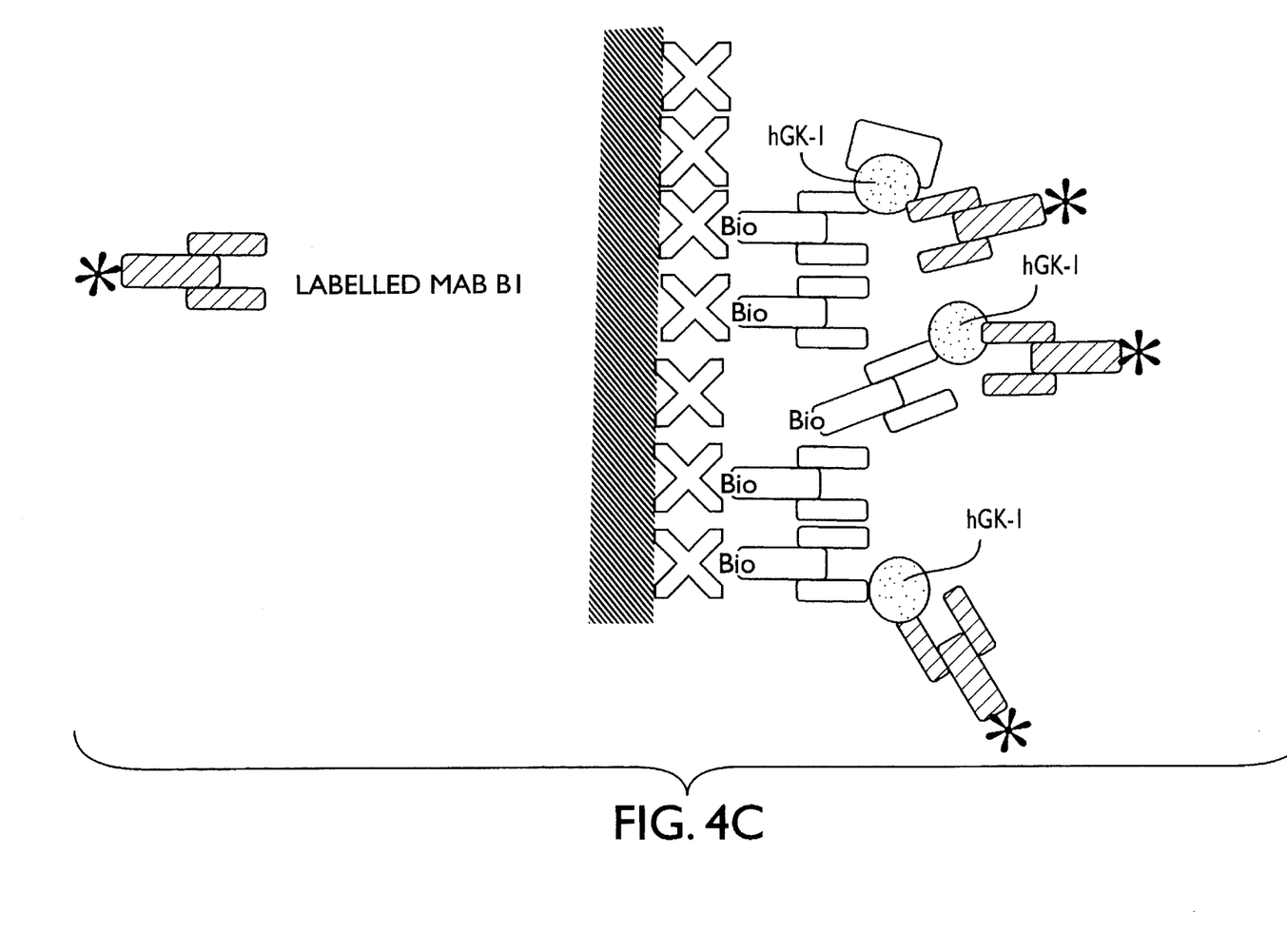

243 samples with no documented clinical back-ground data but consisting of a mixture of normal, BPH and CAP specimens were assayed with hGK-1 assay (FIG. 4) and the results were compared with the PSA+hGK-1 assay in which the blocking monoclonal anti-PSA antibody A5 that did not cross-react with hGK-1 had been omitted. The samples were classified in four different categories based on their PSA-T concentration. The mean of the PSA-T+hGK-1 concentration was calculated as well as the mean proportion (%) of hGK-1 contained in the samples as measured by the hGK-1 assay (Table 3). According to the results the proportion of hGK-1 contained in the samples relative to that of PSA-T ranges from 1–3% although a slight percentual increase is observed at higher PSA-T concentrations.

TABLE 3

Determination of hGK-1 concentrations in serum

| PSA-T range, µg/L | n | PSA-T + hGK-1 mean, µg/L | sd, µg/L | % of hGK-1 mean, % | sd, % |
|---|---|---|---|---|---|
| 1–4 | 40 | 2.0 | 0.75 | 1.0 | 2.9 |
| 4–10 | 89 | 6.3 | 1.7 | 1.3 | 3.6 |
| 10–50 | 69 | 21.9 | 10.2 | 2.1 | 3.9 |
| >50 | 35 | 311.5 | 600.0 | 3.0 | 3.1 |

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

We claim:

1. A bioaffinity assay of prostate-specific antigen (PSA) comprising the measurement in a body fluid sample of either the concentration of total PSA (PSA-T) and the concentration of free form of PSA (PSA-F), or the concentration of total PSA (PSA-T) and the concentration of PSA complexed to alpha-1-antichymotrypsin (PSA-ACT), PSA-T being the sum of PSA-F and PSA-ACT, said method additionally comprising the measurement in a body fluid sample of the concentration of human glandular kallikrein (hGK-1), wherein the concentrations of PSA-T and hGK-1 can be measured in one single assay or in separate assays, and the sum of the concentrations of PSA-T and hGK-1 is used to determine the ratio
    a) PSA-F/(PSA-T+hGK-1) and/or b) PSA-ACT/(PSA-T+hGK-1).

2. A bioaffinity assay according to claim 1 wherein the ratio PSA-F/(PSA-T+hGK-1) is used to differentiate patients with cancer of the prostate (CAP) from patients with benign prostatic hyperplasia (BPH) or normal male subjects without CAP.

3. A bioaffinity assay according to claim 1 wherein the ratio PSA-ACT/(PSA-T+hGK-1) is used to differentiate patients with cancer of the prostate (CAP) from patients with benign prostatic hyperplasia (BPH) or normal male subjects without CAP.

4. A bioaffinity assay according to claim 1 wherein the sum of the concentrations of PSA-T and hGK-1 is measured simultaneously by using antibodies or genetically constructed antibody fragments that recognize common epitopes on both PSA and hGK-1.

5. A bioaffinity assay according to claim 4 wherein a non-competitive bioaffinity assay is used employing at least two different monoclonal antibodies, polyclonal antibodies, a combination of monoclonal and polyclonal antibodies or genetically constructed antibody fragments.

6. A bioaffinity assay according to claim 1 wherein the concentrations of PSA-T and hGK-1 are measured separately after which the sum of the amount of PSA-T and hGK-1 is calculated.

7. A bioaffinity assay according to claim 6 wherein the concentration of hGK-1 is measured by employing two different monoclonal antibodies or antibody fragments in a non-competitive assay and a third monoclonal antibody or antibody fragment to block the reaction of PSA-T with the two monoclonal antibodies or antibody fragments used in the non-competitive assay.

8. An assay according to claim 1 wherein said body fluid sample is serum.

9. An assay according to claim 1 wherein said body fluid sample is plasma.

10. An assay according to claim 1 wherein said body fluid sample is blood.

11. An assay according to claim 1 wherein said body fluid sample is seminal fluid.

12. An assay according to claim 2 wherein said body fluid sample is serum.

13. An assay according to claim 2 wherein said body fluid sample is plasma.

14. An assay according to claim 2 wherein said body fluid sample is blood.

15. An assay according to claim 2 wherein said body fluid sample is seminal fluid.

16. An assay according to claim 3 wherein said body fluid sample is serum.

17. An assay according to claim 3 wherein said body fluid sample is plasma.

18. An assay according to claim 3 wherein said body fluid sample is blood.

19. An assay according to claim 3 wherein said body fluid sample is seminal fluid.

20. An assay according to claim 4 wherein said body fluid sample is serum.

21. An assay according to claim 4 wherein said body fluid sample is plasma.

22. An assay according to claim 4 wherein said body fluid sample is blood.

23. An assay according to claim 4 wherein said body fluid sample is seminal fluid.

24. An assay according to claim 5 wherein said body fluid sample is serum.

25. An assay according to claim 5 wherein said body fluid sample is plasma.

26. An assay according to claim 5 wherein said body fluid sample is blood.

27. An assay according to claim 5 wherein said body fluid sample is seminal fluid.

28. An assay according to claim 6 wherein said body fluid sample is serum.

29. An assay according to claim 6 wherein said body fluid sample is plasma.

30. An assay according to claim 6 wherein said body fluid sample is blood.

31. An assay according to claim 6 wherein said body fluid sample is seminal fluid.

32. An assay according to claim 7 wherein said body fluid sample is serum.

33. An assay according to claim 7 wherein said body fluid sample is plasma.

34. An assay according to claim 7 wherein said body fluid sample is blood.

35. An assay according to claim 7 wherein said body fluid sample is seminal fluid.

* * * * *